(12) United States Patent
Nielsen et al.

(10) Patent No.: US 7,596,202 B2
(45) Date of Patent: Sep. 29, 2009

(54) IMAGING METHOD WITH FILTERED BACK PROJECTION

(75) Inventors: Tim Nielsen, Hamburg (DE); Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 480 days.

(21) Appl. No.: 10/596,470

(22) PCT Filed: Dec. 6, 2004

(86) PCT No.: PCT/IB2004/052665

§ 371 (c)(1),
(2), (4) Date: Jan. 30, 2007

(87) PCT Pub. No.: WO2005/059840

PCT Pub. Date: Jun. 30, 2005

(65) Prior Publication Data

US 2007/0280404 A1    Dec. 6, 2007

(30) Foreign Application Priority Data

Dec. 16, 2003   (EP)   ................................. 03104703

(51) Int. Cl.
*A61B 6/03*   (2006.01)
(52) U.S. Cl. .......................................... 378/4; 378/901
(58) Field of Classification Search ..................... 378/4, 378/901
See application file for complete search history.

(56) References Cited

U.S. PATENT DOCUMENTS

| | | | |
|---|---|---|---|
| 5,311,428 A | 5/1994 | Hayes et al. | |
| 5,982,845 A | 11/1999 | Sidoti et al. | |
| 6,038,282 A | 3/2000 | Wiesent et al. | |
| 7,447,295 B2 * | 11/2008 | Hoheisel et al. | 378/4 |
| 2002/0122529 A1 | 9/2002 | Heuscher | |
| 2002/0177773 A1 | 11/2002 | Natterer et al. | |
| 2003/0161443 A1 | 8/2003 | Xiao et al. | |
| 2005/0058240 A1 * | 3/2005 | Claus | 378/22 |

FOREIGN PATENT DOCUMENTS

DE    44 23 047 A1    1/1996

OTHER PUBLICATIONS

Andia, B.I., et al.; Nonlinear Sinogram Filter Design for Backprojection Reconstruction; 2001; IEEE Proc. of Nuclear Science Symposium Conference; vol. 2; pp. 15179-15183.
Farquhar, T.H., et al.; An Investigation of Filter Choice for Filtered Back-Projection Reconstruction in PET; 1997; IEEE Proc. of Nuclear Science Symposium Conference; vol. 2; pp. 1042-1046.
Kim, J.H., et al.; A Filtering Algorithm based on SPECT Lesion Detectability Potential; 1997; IEEE Proc. of Nuclear Science Symposium Conference; vol. 2; pp. 1706-1710.

* cited by examiner

*Primary Examiner*—Edward J Glick
*Assistant Examiner*—John M Corbett (57) ABSTRACT

The invention relates to an imaging method, in which a projection data record of an examination area to be reconstructed is generated by acquiring projections from different projection directions, in particular with the aid of a computer tomograph. For each projection direction, a filter operator is determined that is optimally adapted to a projection geometry allocated to the respective projection direction. An image of the examination area is reconstructed from the projection data record by filtering the projections with the filter operators determined and by back projection of these filtered projections.

9 Claims, 3 Drawing Sheets

IMAGING METHOD WITH FILTERED BACK PROJECTION

The invention relates to an imaging method in which a projection data record of an examination area to be reconstructed is generated by acquiring projections from different projection directions, in particular with the aid of a computer tomograph, and an image of the examination area is reconstructed from this projection data record with the aid of a filtered back projection. The invention also relates to a computer tomograph for carrying out the method as well as a computer program for controlling the computer tomograph.

Projection data records can be generated by the known methods of the type mentioned at the outset, for example, with a positron emission tomograph (PET), single photon emission computed tomography (SPECT), a C-arm system or a computer tomograph.

In a computer tomograph, the examination area is penetrated by a beam cluster, measured values which depend on the intensity of the beam cluster beyond the examination area are detected and a computer tomography image (CT image) is reconstructed from these measured values with the aid of a filtered back projection. The spatial distribution of the absorption or the attenuation of the radiation in the examination area can be reconstructed by means of a filtered back projection.

The filtered back projection has the advantage that it requires low outlay for computing in comparison to other reconstruction methods, leads to images with very good quality, allows reconstruction of any sub-areas of the examination area and simultaneous processing of different projections or measured values, i.e. parallel processing of measured values.

The problem with filtered back projection is the determination of the filter, which leads to images with optimum image quality for specific projection geometries (in computer tomography, for example, defined by the course of the beams of a projection). The corresponding filter can be analytically determined, for example, by experiments with different filters or with a very high outlay. As the analytical determination of the filter is very difficult, for many projection geometries (in computer tomography, for example, for beam courses, which are generated by helical trajectories with any table feed per rotation and a conical beam cluster), filters have been determined which only inadequately and approximately take into account the respective projection geometry and this leads to reconstructed images rich in artifacts.

An object of the present invention is therefore to provide an imaging method, a computer tomograph and a computer program, in which an optimum filter for the respective projection geometry is determined and used to reconstruct an image, so that images of very good image quality are generated for each projection geometry.

This object is achieved according to the invention by an imaging method comprising the steps:

a) generating a projection data record of an examination area to be reconstructed by acquiring projections from different projection directions, in which a projection direction is allocated to each projection and a projection geometry is allocated to each projection direction, b) providing an iteration operator, which is dependent on a first projection direction, a second projection direction and a filter operator allocated to the second projection direction, and determining, in each case, a filter operator for each projection direction, the filter operations being adapted such that an averaging over all iteration operators that have the same first projection direction but different second projection directions substantially produces an identity operator and in which, on application of an iteration operator to a projection the following operations are carried out:

back projection of the projection in a projection geometry, which is allocated to the first projection direction, forward projection of the back-projected values in a projection geometry, which is allocated to the second projection direction, filtering the forward-projected values with a filter operator of the second projection direction, back projection of the filtered values in a projection geometry, which is allocated to the second projection direction, forward projection of the filtered, back-projected values in a projection geometry which is allocated to the first projection direction, c) reconstruction of an image of the examination area from the projections with the aid of a filtered back projection, the filter operator of the corresponding projection direction being applied to each projection.

Each projection has a plurality of measured values that can be allocated to the respective projection direction. The projection geometry allocated to each projection describes how a forward and back projection can be carried out for this projection or the corresponding projection direction. This is described in more detail below by way of example for a computer tomograph.

The back projection can be described by a back projection operator, that projects a projection from a projection space into the examination area. A projection space may, for example, in the case of a computer tomograph, be a space that is spanned by the detector face and the beam source position. The forward projection may be described by a forward projection operator that projects forward from the examination area into the projection space. Alternatively, an operator may also be defined which consecutively carries out a back and forward projection. This operator reproduces a projection from the projection space into said space and can replace the corresponding combination of back and forward projection operators.

The determination of a filter operator described in step b) leads to an optimum filter adapted to the respective projection geometry that, after reconstruction by means of a filtered back projection, leads to images with very good quality. This leads, in particular, in the case of projection geometries, for which until now only approximation solutions for filters have been known, to an improved image quality compared to the prior art.

The iterative embodiment described in claim 2 allows the determination of optimum filter operators in a mathematically relatively simple manner so the computing outlay is further reduced.

Claim 3 describes an embodiment in which a CT image is reconstructed from a projection data record that is generated with the aid of a computer tomograph and that has improved image quality compared to known computer tomography methods.

Claim 4 describes an embodiment in which the filter operator is the same for all projection directions. This leads to reduced outlay for computing with unchanged good image quality.

The reconstruction according to the invention of the examination area from a projection data record that has been generated with a PET or a SPECT as claimed in claim 5, leads to images with very good quality.

The discretization of at least some operators as claimed in claim 6 allows uncomplicated, relatively simple implementation of the method according to the invention.

Presenting at least some operators by linear functionals as claimed in claim 7 leads to an exact calculation of the filter operators and therefore to further improved image quality.

A computer tomograph for carrying out the method according to the invention is described in claim 8.

Claim 9 defines a computer program for controlling a computer tomograph as claimed in claim 8.

The invention will be described in more detail hereinafter with the aid of the drawings, in which.

Figure 1:
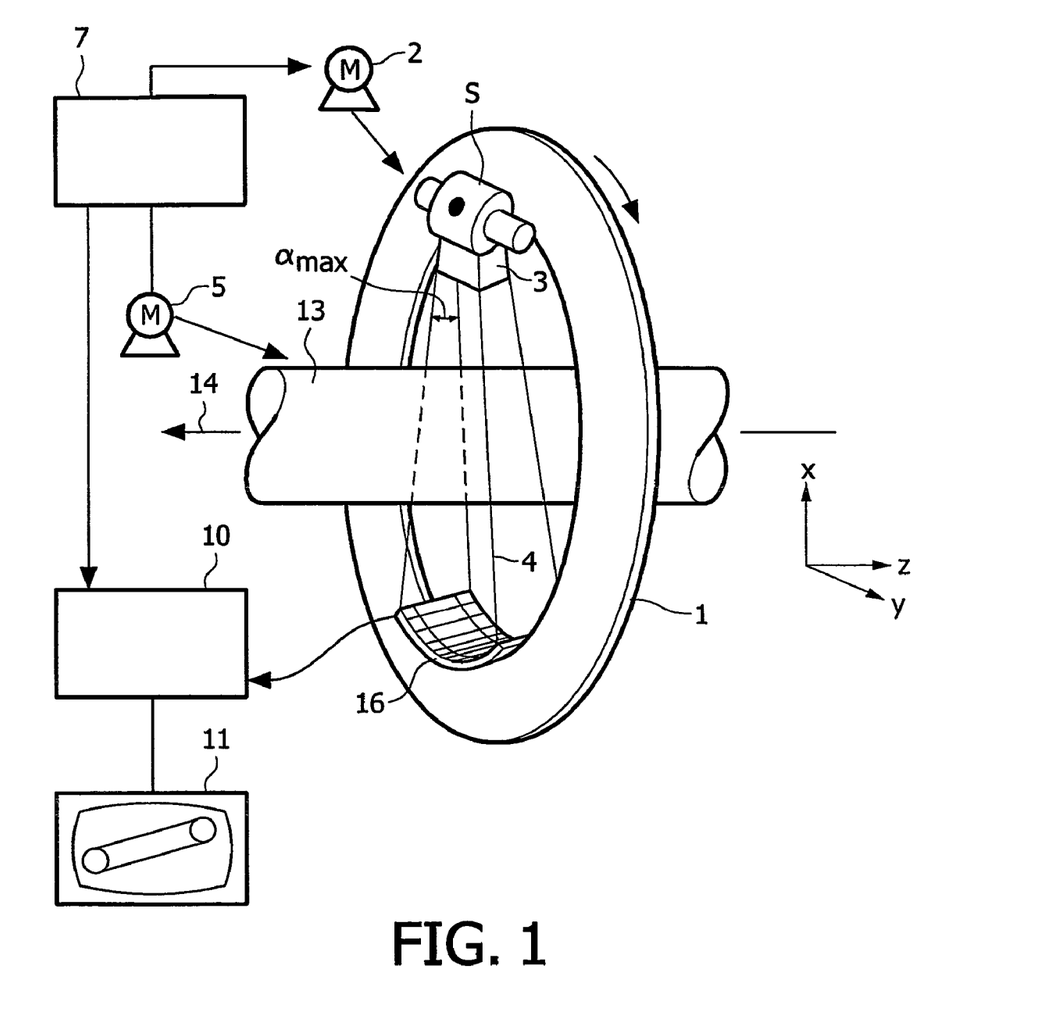
FIG. 1 shows a computer tomograph, with which the method according to the invention can be carried out.

The computer tomograph shown in FIG. 1 comprises a gantry 1 which can rotate about an axis of rotation 14 extending parallel to the z-direction of the coordinate system shown in FIG. 1. For this purpose, the gantry 1 is driven by a motor 2 at a preferably constant, but adjustable angular speed. Fastened to the gantry 1, is a beam source S, for example an X-ray source. Said X-ray source is provided with a collimator arrangement 3 which blanks out from the radiation generated by the beam source S, a conical beam cluster 4, i.e. a beam cluster that has an endless extent, that differs from zero, in the z-direction and in a direction perpendicular thereto (i.e. in a plane perpendicular to the axis of rotation). Alternatively a fan-shaped beam could also be used.

The beam cluster 4 penetrates a cylindrical examination area 13, in which an object (not shown) is located.

After passing through the examination area 13, the beam cluster 4 meets a detector unit 16 with a detector face fastened to the gantry 1, which detector face comprises a large number of detector elements which are arranged in a matrix shape in rows and columns in this embodiment. The detector columns preferably extend parallel to the axis of rotation 14. The detector rows are located in planes perpendicular to the axis of rotation, in this embodiment, on an arc of a circle around the beam source S (focus-centered detector). In other embodiments, however, they may be formed differently, for example describe an arc of a circle around the axis of rotation 14 or be straight. Each detector element met by the beam cluster 4 supplies a measured value in each position of the beam source for a beam from the beam cluster 4. If a fan-shaped beam cluster is used in other embodiments, the detector unit could also have only one detector line.

The angular aperture designated by $\alpha_{max}$, of the beam cluster 4 determines the diameter of the object cylinder, within which the object to be examined is located during acquisition of the measured values. In this instance, the angular aperture is defined as the angle that a beam located in a plane perpendicular to the axis of rotation 14 at the edge of the beam cluster 4, encloses with a plane defined by the beam source S and the axis of rotation 14. The examination area 13 and the object or the patient mounting table can be displaced parallel to the axis of rotation 14 or to the z-axis by means of a motor 5. Equivalently to this, however, the gantry could also be displaced in this direction. If a technical object is involved and not a patient, the object can be rotated during the examination, while the beam source S and the detector unit 16 remain still.

With the aid of the motors 2 and 5, the beam source S and the detector unit 16 may describe a trajectory relative to the examination area 13, which extends on an imaginary cylinder surface. This trajectory may, for example, extend helically when the two motors are in operation. If, on the other hand, the motor 5 for the feed in the direction of the axis of rotation 14 is out of action and the motor 2 causes the gantry to rotate, a circular trajectory is produced for the beam source S and the detector unit 16 relative to the examination area 13.

The measured values acquired from the detector unit 16 are fed to a reconstruction unit, in particular a reconstruction computer 10 which is connected to the detector unit 16, for example via a wireless data transmission device (not shown). The reconstruction unit 10 reconstructs a distribution of attenuation values, for example an absorption distribution, in the examination area 13 and reproduces them, for example on a monitor 11. The two motors 2 and 5, the reconstruction unit 10, the beam source S and the transfer of the measured values from the detector unit 16 to the reconstruction unit 10 are controlled by the control unit 7.

In other embodiments, the acquired measured values can be firstly fed for reconstruction to one or more reconstruction computers, which pass the reconstructed data, for example, via a glass fiber cable to an image processing computer.

Figure 2:
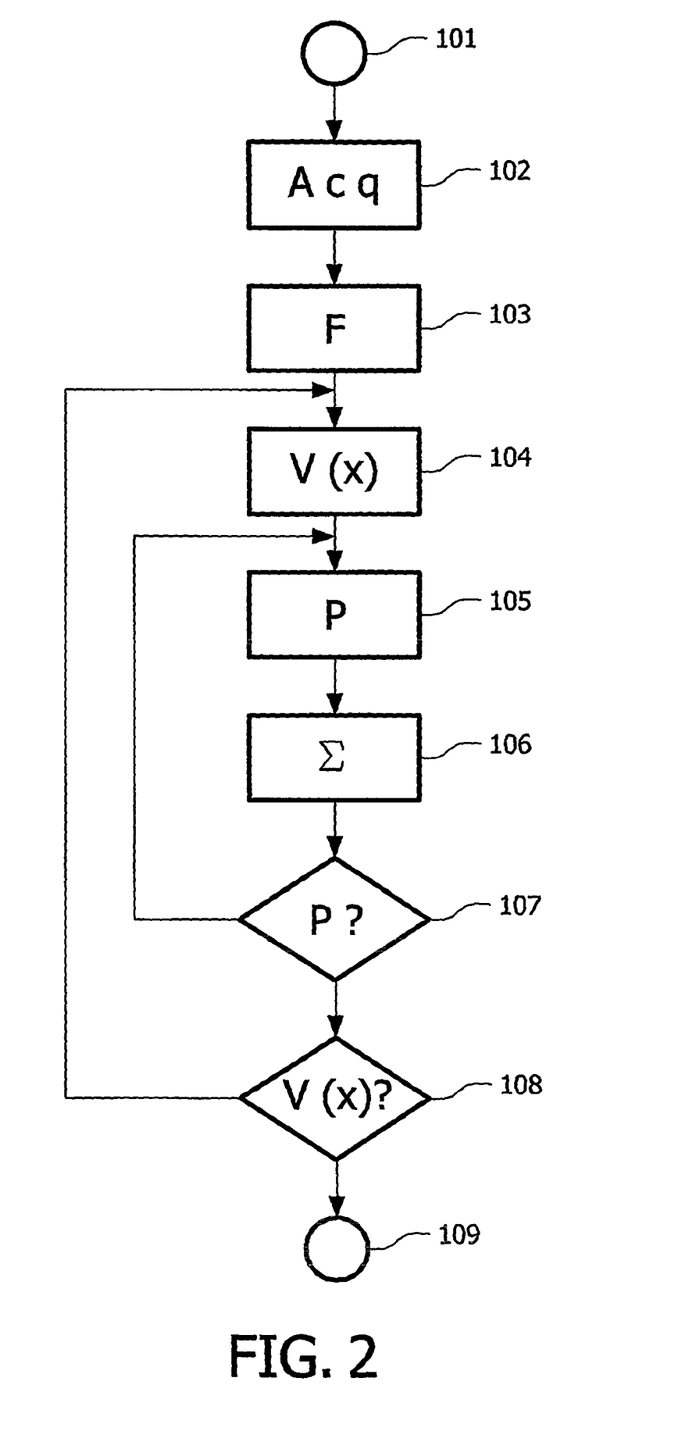
FIG. 2 shows a flow chart of the method according to the invention and FIG. 3 shows a flow chart of the determination of filter operators according to the invention.

FIG. 2 shows the flow of a measuring and reconstruction method, which can be carried out with the computer tomograph as claimed in FIG. 1.

After the initialization in step 101, the gantry rotates at an angular speed that is constant in this embodiment. It may vary however, for example as a function of the time or the beam source position.

The examination area 13 and the object or the patient mounting table is displaced parallel to the axis of rotation 14 in step 102 and the radiation of the radiation source S is switched on, so the detector unit 16 can detect the radiation from a large number of angular positions.

In step 103, the measured values are filtered, in that a filter operator is applied to the measured values. The filtering of the measured values can be described by the following equation:

$$\tilde{p}_i = F_i p_i \quad (1)$$

Here $p_i$ is one of the projections acquired in step 102, a projection being the quantity of all measured values that have been acquired at a specific beam source position. Each projection may be allocated a projection direction that is defined by the respective beam source position and the center of the detector face. The index "i" therefore distinguishes different beam source positions or projection directions. Furthermore $F_i$ is the filter operator that is allocated to the beam source position or the projection direction of the projection $p_i$ and $\tilde{p}_i$ is the corresponding filtered projection.

To better understand the following steps, a mathematical description is inserted which leads to a conditional equation for the filter operators $F_i$. This mathematical description is carried out here for a computer tomograph, without being limited thereto. This description is transferable in a similar manner to all methods with which a projection data record of an examination area can be generated by acquiring projections from different projection directions, as is the case, for example in PET or SPECT. For transfer to methods of this type, "beam source position" has to be replaced hereafter by "projection direction". Moreover, in PET or SPECT, no distribution of attenuation values would, of course, be reconstructed, but a distribution of activity values. Furthermore, corresponding, known forward and back projection operators would have to be used, in particular in PET and SPECT methods.

The following equations apply:

$$P_i B_i = \text{id and} \tag{2}$$

$$p_i = P_i \mu, \tag{3}$$

in which $P_i$ is a forward projection operator which, applied to a distribution $\mu$ of attenuation or absorption values in the examination area 13, that describe the attenuation or absorption of the beams, projects these values forward along beams of the i-th beam source position, so a projection $p_i$ is produced. The forward projection operator therefore describes a measuring process. The back projection operator $B_i$ projects a projection back into the examination area along beams of the i-th beam source position. If a projection is now projected back along the same beams and projected forwards, the original projection is produced, therefore equation (2) applies, wherein id is an identity operator. This means that id applied to a projection does not change it.

The filtered back projection can be described by $$\tilde{\mu} = \frac{1}{N} \sum_i B_i F_i p_i \tag{4}$$

in which $\tilde{\mu}$ is the reconstructed image and N is the number of beam source positions, at which measured values or projections have been acquired, which are used for the reconstruction. The object of the reconstruction consists in generating a CT image with the aid of the measured projections in such a way that an application of a forward projection operator to the reconstructed attenuation values of the CT image leads to the originally measured projections for each beam source position. If this condition is adequately fulfilled, the attenuation value distribution of the object has been exactly reconstructed. A filter, which at least substantially fulfils this condition, is an optimum filter in the sense of the invention. This means that the following equation should be fulfilled for each beam source position j.

$$P_j \tilde{\mu} = p_j. \tag{5}$$

The indices i and j can denote each respective beam source position that is used for the reconstruction. They were selected differently in order to be able to differentiate a first beam source position or projection direction j from a second beam source position or projection direction i below in the description.

Reference is made to the fact that this mathematical description assumes that ideal projections or measured values exist, i.e. measured values which, for example, have not been changed by noise or beam hardening. Equation (5) applies exactly for these ideal measured values. If the measured values are changed, for example, by noise or beam hardening, which is the case in real measured values, equation (5) is only substantially fulfilled even for an optimum filter operator.

Insertion of equation (3) in equation (5) results in $$P_j \frac{1}{N} \sum_i B_i F_i p_i = p_j, \tag{6}$$

and insertion of equation (3) in equation (6) leads to $$P_j \frac{1}{N} \sum_i B_i F_i P_i \mu = P_j \mu. \tag{7}$$

As equation (7) applies to any distribution $\mu$ of attenuation values, the operators used for this distribution also have to be the same:

$$P_j \frac{1}{N} \sum_i B_i F_i P_i = P_j. \tag{8}$$

This equation is equivalent to $$P_j \frac{1}{N} \sum_i B_i F_i P_i B_j = P_j B_j. \tag{9}$$

Finally, insertion of equation (2) in equation (9) leads to the following conditional equation for the filter operators $F_i$:

$$\frac{1}{N} \sum_i I_{j,i} = \frac{1}{N} \sum_i P_j B_i F_i P_i B_j = \text{id}. \tag{10}$$

Each filter operator $F_i$, that at least approximately fulfils equation (10), can be applied according to the invention.

In the scope of the invention $I_{j,i} = P_j B_i F_i P_i B_j$ is designated as an iteration operator, so the designation of the operator $I_{j,i}$ is compatible with the special embodiment described below which iteratively determines filter operators $F_i$, that fulfill the equation (10).

As the back projection and forward projection operators depend exclusively on the projection geometry, i.e. the course of the beams starting from the respective beam source position or, and this is the same, on the respective beam source position, the form of the beam cluster and on the arrangement of the detector elements of the detector unit, but not on the measured values themselves, the filter operators only have to be determined once for a specific projection geometry. In the case of further measurements with the same projection geometry, the filter operators already determined can be used.

Each method that is suitable for determining the filter operators $F_i$, that fulfill the equation (10), can be used according to the invention. For example, the operators $P_i B_j$, $P_j B_i$ and $F_i$ can be shown in each case as a matrix, in which the operators $P_i B_j$ and $P_j B_i$ or their matrix elements can be determined by simple geometric observations from the given projection geometry. When the operators are shown in this way equation (10) provides a linear equation system, in which only the matrix elements of the filter operator $F_i$ are unknown. This equation system can be solved by known methods.

Alternatively, equation (10) can be solved iteratively by means of the following iteration equation:

$$F_j^{k+1} = F_j^k + \text{id} - \frac{1}{N} \sum_i P_j B_i F_i^k P_i B_j. \tag{11}$$

Here $F_j^k$ is the filter operator of the j-th beam source position, which is allocated to the k-th iteration step. Accordingly, $F_j^{k+1}$ is the filter operator of the j-th beam source position, which is allocated to the (k+1)-th iteration step. A respective identity operator can be used, for example, as the start operator $F_j^0$ for the filter operators.

Figure 3:
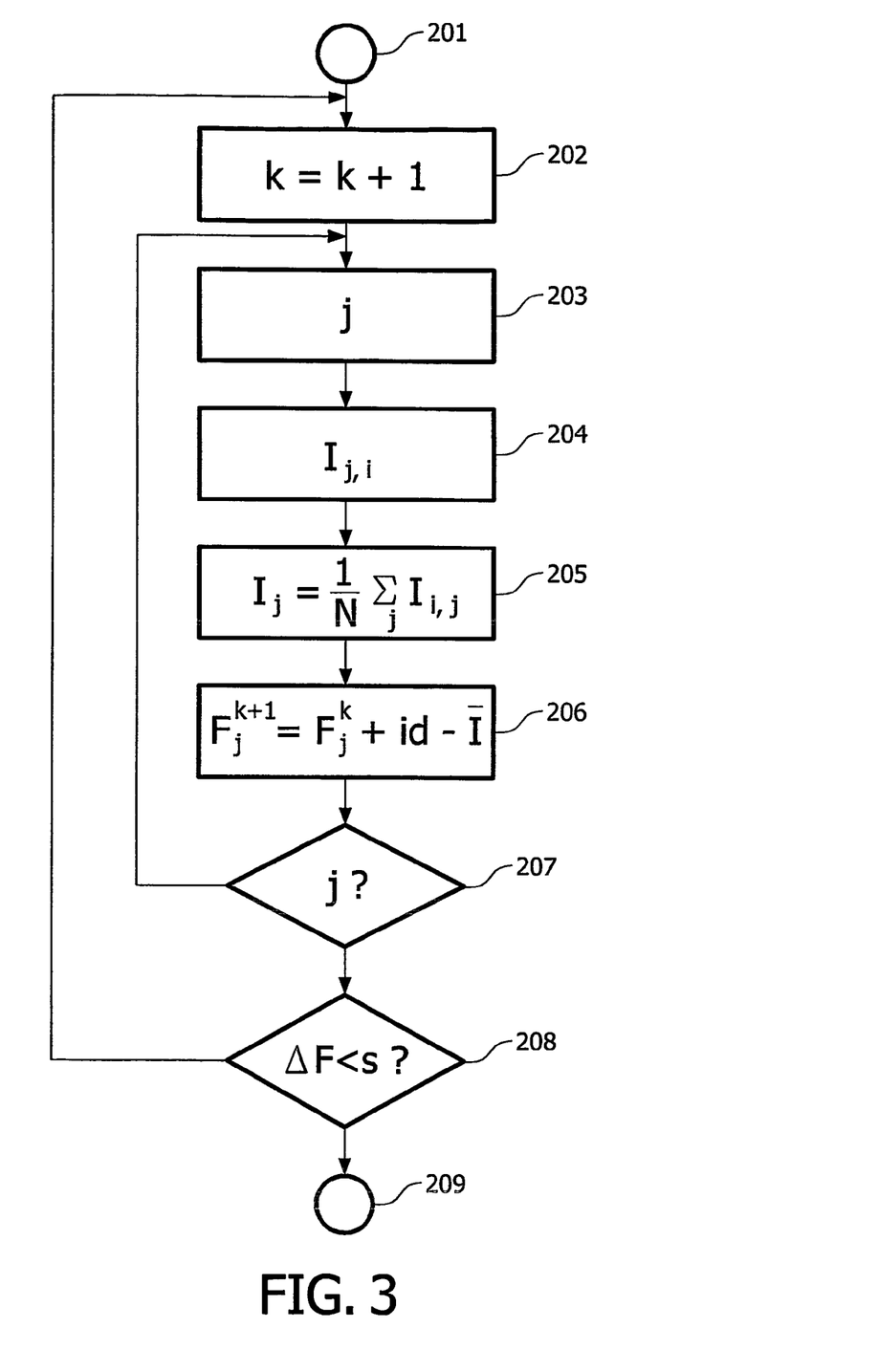

Furthermore, determination of the optimum filter for the respective projection geometry is shown with the aid of the flow chart shown in FIG. 3, which substantially complies with equation (11). Each operator is shown as a matrix here.

In step 201, a matrix, for example a unit matrix, is provided initially for each filter operator $F_j$. The matrices for back and forward projections can be determined for the respective projection geometry by simple geometric considerations. In computer tomography, in the simplest case, when the part to be reconstructed of the examination area (field of view-FOV) is divided into a plurality of voxels and each voxel contains an attenuation value, the forward projection operator can add up the attenuation values of the voxels which are penetrated by a beam of a projection, to form a measured value. The pertaining matrix would then have ones at the corresponding positions and otherwise zeros. The back projection operator may then, for example, be designed such that, proceeding from a measured value of a projection, the respective measured value is added proportionally to all attenuation values, the voxel of which has been penetrated by the beam that has caused the measured value. The pertaining matrix also consists of ones and zeros which are arranged in the matrix such that, when the matrix is applied to a projection, the above-described addition of measured values to the corresponding attenuation values is carried out. The invention is, of course, not limited to the two simple examples of a back and forward projection operator.

Alternatively, operators can also be defined that consecutively carry out a back and forward projection (see, for example, equation (19)). These operators can be used instead of a back and a forward projection operator. These operators reproduce a projection from a projection space into the same projection space.

Once the back and forward projection operators have been determined and filter operators $F_j^0$ have been specified as starting values in step 201, an iteration step is carried out in steps 202 to 207. For this purpose, in step 202, an iteration numerator k, which, for example, initially equals zero, is increased by one.

In step 203, a beam source position j is selected for which no filter operator $F_j^{k+1}$ has been determined yet in the current iteration step (k+1). In the first iteration step (k=1), this may, for example, be the temporary first beam source position.

In step 204, an iteration operator $$I_{j,i}^k = P_j B_i F_i^k P_i B_j \qquad (12)$$

is determined for the beam position j and each beam source position i, in each case, in which $F_i^k$ is the filter operator of the i-th beam source position that has been determined in the previous iteration step. If step 204 is firstly carried out, the filter operator $F_i^k$ equals the filter operator specified initially in step 201.

The i-th beam source position corresponds to the second projection direction and the j-th beam source position corresponds to the first projection direction according to claim In step 205, averaging is carried out over all the iteration operators calculated in step 204. The average value may, for example, be determined as an arithmetic average: 1.

$$\bar{I}_j^k = \frac{1}{N} \sum_i I_{j,i}^k. \qquad (13)$$

Alternatively, other average values could be used. Moreover, if it were assumed, that measured values are acquired continuously, that there are therefore no discrete beam source positions, calculation of the average value with a sum equation according to equation (13) could be replaced by a corresponding integral equation.

The filter operator $F_j^{k+1}$ of the j-th beam source position of the current (k+1)-th iteration step can then be calculated in step 206 by means of the equation $$F_j^{k+1} = F_j^k + id - \bar{I}_j^k \qquad (14).$$

This means that the average iteration operator calculated previously in step 205 is subtracted from the sum of the corresponding filter operator of the previous iteration step $F_j^k$, which equals the initial filter operator when this step is first carried out, and the identity operator.

In step 207, a check is made as to whether a filter operator $F_j^{k+1}$ has already been determined for each beam source position j in this iteration step. If this is not the case step 203 is proceeded with. Otherwise step 208 follows.

A check is made in step 208 as to whether an abort criterion is fulfilled for the determination of the filter operators. The abort criterion may, for example, use each measure that determines the deviation of the filter operators of the current iteration step from the filter operators of the previous step. If this deviation is smaller than an established threshold value s, the iteration method can be terminated. The abort criterion may then appear, for example, as follows:

$$s > \sum_{j,t} \left| (F_j^{k+1})_t - (F_j^k)_t \right|. \qquad (15)$$

$(F_j^{k+1})_t$ or $(F_j^k)_t$ are the t-th matrix element of the respective filter operator here. Furthermore, the abort criterion may also have a predeterminable number of iteration steps, the iterative determination of the filter operators being terminated when this number is reached or exceeded.

If the abort criterion is met, determination of the filter operators in step 209 ends, otherwise a further iteration step is proceeded with in step 202.

Once the filter operators have been determined and the projections filtered according to equation (1) (step 103 in FIG. 2), the computer tomography method according to the invention can be continued with in step 104.

For this purpose, a voxel V(x) is determined within the FOV in step 104. Then a projection is selected in step 105 that is not yet used for reconstruction of the voxel V(x). If no beam of the projection runs centrally through the voxel V(x) it is determined at which position a central beam would have met the detector face. The associated measured value is then calculated by interpolation of the measured values of adjacent beams. The measured value that can be allocated to the beam of the projection passing through the voxel centrally, or the corresponding measured value obtained by interpolation, is accumulated on the voxel V(x) in step 106. In step 107, a check is made as to whether all projections have been observed. If this is not the case, the flow chart branches to step 105. Otherwise a check is made in step 108, whether all voxels V(x) have been passed through in the FOV. If this is not the case, step 104 is proceeded with. If, on the other hand, all voxels V(x) in the FOV have been passed through, the distribution of the attenuation values, i.e., for example, the absorption values, has been determined in the entire FOV, and the computer tomography method according to the invention is ended (step 109).

If the trajectory, on which the beam source S moves relative to the examination area 13, runs such that the operator combination $P_jB_i$ is the same for all beam source positions i and j that have the same spacing on the trajectory, the equation (11) is simplified to $$F^{k+1} = F^k + id - \frac{1}{N}\sum_i P_1 B_i F^k P_i B_1. \quad (16)$$

This means that each beam source position has the same filter operator, so that steps 203 and 207 can be dispensed with and j, for example, as in equation (16), may equal one. This substantially reduces the outlay for computing to determine the filter operators. This possible simplification occurs, in particular, in circular or helical trajectories.

In the above-described embodiment, the operators are shown by matrices. The filtering of a projection p by means of a filter operator F can therefore be described in a known manner by the following equation:

$$(Fp)_r = \sum_{l=1}^{m} F_{r,l} p_l. \quad (17)$$

Here m is the number of measured values per projection, in other words, for example, the number of detector elements, and $(Fp)_r$ is one of the filtered measured values of the projection p. Alternatively, the operators could also be shown analytically however:

$$(Fp)(\phi') = \int_{\Re^2} f(\phi', \phi) p(\phi) d\phi \quad \forall \phi' \in \Re^2 \quad (18)$$

and $$(P_iB_jp)(\phi') = \int_{\Re^2} \gamma_{i,j}(\phi', \phi) p(\phi) d\phi \quad \forall \phi' \in \Re^2 \quad (19)$$

Here $(Fp)(\phi')$ is a filtered projection at the position $\phi'$ on the detector face, $p(\phi)$ is an unfiltered projection at the position $\phi$ on the detector face and $f(\phi', \phi)$ is a filter kernel function which describes the filtering in equation (18). Furthermore, $(P_iB_jp)(\phi')$ designate a projection that has initially been back-projected and then forward-projected, at the position $\phi'$ on the detector face and $\gamma_{i,j}(\phi', \phi)$ a projection kernel function. The corresponding iteration equation for these analytical operators to determine the filter kernel function $f(\phi',\phi)$ is:

$$f_j^{k+1}(\phi', \phi) = f_j^k(\phi', \phi) + \delta(\phi' - \phi) - \\ \frac{1}{N}\sum_i \int\int \gamma_{j,i}(\phi', \xi) f_j^k(\xi, \eta) \gamma_{i,j}(\eta, \phi) d\xi d\eta \quad (20)$$

$\delta(\phi'-\phi)$ is the delta function here. The projection kernel function could be calculated in step 201 by simple geometric consideration on the basis of the predetermined projection geometry. In step 204, different iteration operators $I_{j,i} = \int\int \gamma_{j,i}(\phi',\xi) f_j^k(\xi,\eta)\gamma_{i,j}(\eta,\phi)d\xi d\eta$ would then be determined, according to which an average value $\bar{I}_j$ is calculated in step 205 by averaging over iteration operators with a predetermined fixed j. In step 206, the filter kernel function $f_j^{k+1}(\phi',\phi)$ of the (k+1)-th iteration step for the j-th beam source position according to equation (20) is then determined by subtracting the average value $\bar{I}_j$ from the sum of the corresponding filter kernel function of the k-th iteration step and the delta function.

The analytical calculation of the filter kernel function has the advantage that, in comparison to carrying out the filter operator determination with discrete operators, for example as described above with matrices, no interpolation caused by discretization is required and it is therefore more exact.

As the measured values of a projection are generally arranged on the detector face at the positions of the corresponding detector elements, the determined filter kernel function $f(\phi',\phi)$ has to be discretized. It can be converted into a matrix, so these measured values can be filtered according to equation (17).

The imaging method according to the invention is not limited to computer tomography methods. It may, for example, be applied in a C-arm system, in PET or SPECT.

In known PET methods, gamma quantum pairs occur in the examination area owing to annihilation processes, (an electron and a positron collide and thus generate two gamma quantum's). As the electron and positron are relatively slow prior to the annihilation, the gamma quantum's of a pair, owing to the impulse conservation principle, starting from the site of origin, move in substantially opposite directions, as is known. Arranged around the examination area is a detector ring, which can be detected from the gamma quantum's leaving the examination area. More precisely, coincidences are detected, i.e. the numbers of coincidences per time interval and angle direction are detected. A coincidence here is the substantially simultaneous meeting of two gamma quantum's at positions on the detector ring that are offset from one another substantially by 180°. A detector element measures, with each of the other detector elements, respective coincidences of gamma quantum's which move along the lines defined by the respective detector elements. A specific detector element therefore measures, together with other detector elements, coincidences in the different angle directions. All coincidences measured with the detector element per time interval in the different angle directions may form a projection (in computer tomography this corresponds to a beam fan issuing from a beam source). The projection direction of the projection may then, for example, be defined by the detector element and the center of the detector ring. The back projection and the forward projection for a projection direction in the respective projection geometry can be carried out in a known manner, in which the projection geometry may be defined by the respective projection direction or arrangement of the respective detector element on the detector ring and the geometry of the PETs. The determination according to the invention of filter operators for the respective projection geometry and the subsequent filtered back projection also lead in PET to improved image quality in comparison to known PET methods.

In the two-dimensional PET method described, by means of a detector ring, the same filter operator can be used according to the invention in accordance with equation (16) for each projection direction. As a filter operator then only has to be determined for one projection direction, the outlay for computing is considerably reduced.

In the SPECT method, located in the examination area are radioactive isotopes, which have been injected into the blood stream of a patient located in the examination area. The isotopes decompose under the radiation of gamma quantum's. The gamma quantum's leaving the examination area are measured from different directions by means of a gamma camera with a detector face, i.e. the number of gamma quantum's which meet the detector face per time interval is measured. The measured values, which have been acquired by the detector face at a gamma camera position, can be designated as a projection. The projection direction of a projection may, for example, be the direction that extends through the center of the examination area and through the gamma camera. Back and forward projecting for a projection geometry determined by the geometry of the SPECT and the projection direction are known, so the determination according to the invention of filter operators and the filtered back projection can also be carried out by a SPECT using these filter operators. Images reconstructed in this way show a significantly improved image quality in comparison to known SPECT methods.

Prior to the back projection of the measured values generated by PET or SPECT methods, an absorption correction of the measured values may be carried out in a known manner by means of transmission measurements.

In comparison to known imaging methods, the invention has the advantage that all the measured values and the exact projection geometry for the reconstruction can be used. The method according to the invention therefore shows no artifacts that in known computer tomography methods can be caused by the cone angle in the reconstruction being neglected. The cone angle of a beam is the angle that this beam encloses with a plane oriented perpendicular to the axis of rotation 14. A further advantage of the invention is that the image quality of the reconstructed CT image is very good regardless of the table feed per rotation in a computer tomography method with helical trajectory. In known computer tomography methods, a reconstruction of CT images with very good image quality is only possible for specific table feeds per rotation.

LIST OF REFERENCE NUMERALS $\alpha_{max}$ aperture angle
id identity operator
i,j projection directions
k,k+1 iteration step
$p_j$ projection
$F_i, F_j$ filter operator
$F_j^0$ initial filter operator
$F_i^k$ filter operator of the i-th projection direction and the k-th iteration step
$F_j^{k+1}$ filter operator of the j-th projection direction and the (k+1)-th iteration step
$I_{j,i}$ iteration operator
$I_{j,i}^k$ iteration operator of the k-th iteration step
$\bar{I}_j^k$ average value of the iteration operator of the k-th iteration step
S beam source
1 gantry
2, 5 motor
3 collimator arrangement
4 beam cluster
7 control unit
10 reconstruction unit
11 monitor
13 examination area
14 axis of rotation
16 detector unit

The invention claimed is:

1. An imaging method comprising the steps:
   a) generating a projection data record of an examination area to be reconstructed by acquiring projections from different projection directions, wherein a projection direction is allocated to each projection and a projection geometry is allocated to each projection direction,
   b) providing an iteration operator that is dependent on a first projection direction, a second projection direction and a filter operator allocated to the second projection direction, and determining, in each case, a filter operator for each projection direction, the filter operators being adapted such that an averaging over all iteration operators, that have the same first projection direction but different second projection directions, substantially produces an identity operator and in which, on application of the iteration operator to a projection the following operations are carried out:
      back projection of the projection in a projection geometry, which is allocated to the first projection direction,
      forward projection of the back-projected values in a projection geometry, which is allocated to the second projection direction,
      filtering the forward-projected values with a filter operator of the second projection direction,
      back projection of the filtered values in a projection geometry, which is allocated to the second projection direction,
      forward projection of the filtered, back-projected values in a projection geometry which is allocated to the first projection direction,
   c) reconstruction of an image of the examination area from the projections with the aid of a filtered back projection, in which the filter operator of the corresponding projection direction is applied to each projection.

2. An imaging method as claimed in claim 1, wherein a filter operator is iteratively determined in each case for each projection direction prior to reconstruction, wherein a filter operator is allocated to each iteration step for each projection direction, wherein a plurality of iteration steps are carried out until an abort criterion is fulfilled, and wherein, in an iteration step, all filter operators that are allocated to the iteration step, are determined before the next iteration step is carried out, and in that once an identity operator and, for each projection direction, an initial filter operator have been provided, in an iteration step to determine the filter operator of a specific projection direction that is allocated to the respective iteration step, the following steps are carried out:
   i) provision of an iteration operator which, applied to a projection, carries out the following operations:
      back projection of the projection in a projection geometry, which is allocated to the specific projection direction,
      forward projection of the back-projected values in a projection geometry, which is allocated to the second projection direction,
      filtering the forward-projected values with the filter operator of the second projection direction, which is allocated to the previous iteration step,
      back projection of the filtered values in a projection geometry, which is allocated to the second projection direction,
      forward projection of the filtered, back-projected values in a projection geometry, which is allocated to the specific projection direction, ii) determination of an iteration operator, in each case, for each projection direction, the second projection direction of the respective iteration operator, being the respective projection direction, iii) determination of an average operator by averaging over all iteration operators determined in step ii)

iv) determination of the filter operator of the specific projection direction, which is allocated to the current iteration step, by subtracting the average operator from the sum of the filter operator of the specific projection direction, which is allocated to the previous iteration step, and the identity operator.

3. Imaging method as claimed in claim 1, wherein generation of a projection data record with a computer tomograph in step a) comprises the following steps:

generating a beam cluster penetrating the examination area, with a beam source, generating a relative movement between the beam source, on the one hand, and the examination area, on the other hand, which comprises a rotation about an axis of rotation, in which the beam source adopts different beam source positions, and acquiring measured values that depend on the intensity of beams in the beam cluster beyond the examination area, with a detector unit during the relative movement at different beam source positions, wherein measured values, the beams of which are emitted from the same beam source position, form a projection, a projection direction is allocated to each projection, the projection direction pointing from the respective beam source position to a center of the detector unit, and the projection geometry that is allocated to the respective projection direction, is defined by the respective beam source position and the position of the detector unit and the beam course determined thereby.

4. An imaging method as claimed in claim 3, in which a trajectory, on which the beam source moves relative to the examination area, extends such that an operator which, applied to a projection, projects said projection back along beams of a first beam source position and projects the back-projected values forward along beams of a second beam source position, is the same for first and second beam source positions, which have the same spacing along the trajectory, and, in particular, the trajectory is circular or helical, wherein the same filter operator is used for each projection direction.

5. A computer tomograph for carrying out the method as claimed in claim 3 comprising a beam source for generating a beam cluster penetrating an examination area, a drive arrangement for generating a relative movement between the beam source, on the one hand, and the examination area, on the other hand, which comprises a rotation about an axis of rotation, a detector unit for acquiring measured values that depend on the intensity of beams in the beam cluster beyond the examination area, during the relative movement, a reconstruction unit for reconstructing a computer tomography image of the examination area from the measured values, a control unit for controlling the beam source, the drive arrangement, the detector unit and the reconstruction unit according to the steps as claimed in claim 3.

6. A computer readable medium encoded with a computer program for a control unit for controlling a beam source, a detector unit, a drive arrangement and a reconstruction unit of a computer tomograph for carrying out the steps as claimed in claim 3.

7. An imaging method as claimed in claim 1, wherein the projection data record in step a) is generated with a positron emission tomograph or a single photon emission computer tomograph.

8. An imaging method as claimed in claim 1, wherein at least some of the operators are discretized.

9. An imaging method as claimed in claim 1, wherein at least some of the operators are linear functionals.

* * * * *